United States Patent [19]

Matsumura et al.

[11] 4,338,433
[45] Jul. 6, 1982

[54] MORANOLINE DERIVATIVES AND PROCESS FOR PREPARATION THEREOF

[75] Inventors: Shingo Matsumura, Kyoto; Hiroshi Enomoto, Nagaokakao; Yoshiaki Aoyagi, Kyoto; Yoji Ezure, Otsu; Yoshiaki Yoshikuni, Kyoto; Masahiro Yagi, Kusatsu; Nobutoshi Ojima, Kyoto, all of Japan

[73] Assignee: Nippon Shinyaku Co. Ltd., Japan

[21] Appl. No.: 214,009

[22] Filed: Dec. 8, 1980

[30] Foreign Application Priority Data

Dec. 8, 1979 [JP] Japan .............................. 54-159417
Jun. 6, 1980 [JP] Japan ................................ 55-76838
Sep. 22, 1980 [JP] Japan .............................. 55-131949

[51] Int. Cl.$^3$ .............................................. C08B 37/16
[52] U.S. Cl. ...................................... 536/46; 424/180
[58] Field of Search ........................... 536/46; 424/180

[56] References Cited

U.S. PATENT DOCUMENTS 3,553,191 1/1971 Parmerter et al. .................... 536/46

FOREIGN PATENT DOCUMENTS 54-106595 8/1979 Japan ..................................... 536/46

Primary Examiner—Ronald W. Griffin
Attorney, Agent, or Firm—Jacobs & Jacobs

[57] ABSTRACT

Moranolines are produced which are useful for controlling blood sugar levels.

11 Claims, 6 Drawing Figures

MORANOLINE DERIVATIVES AND PROCESS FOR PREPARATION THEREOF

DETAILED DESCRIPTION OF THE INVENTION

Cyclodextrin glycosyltransferase (E.C.-2,4,1,19 cyclodextrin glycosyltransferase) has an old history, and since this enzyme was discovered for the first time from *Bacillus macerans,* the enzyme is generally called *Bacillus macerans* amylase. As reported in, for example, Japanese Patent Application Laid-Open Specification Nos. 20373/72, No. 63189/75 and No. 88290/75, Hans Bender, Archives of Microbiology, 3, pages 27–282, 1977 and Agricultural and Biological Chemistry, 40, page 753, 1976, it is known that this enzyme is produced by *Bacillus macerans, Bacillus megaterium, Bacillus circulans, Bacillus polymyxa, Bacillus stearothermophillus, Klebsiella pneumoniae* and Bacillus No. 38-2 (alkalophilic bacteria).

Moranoline is represented by the following structural formula (III):

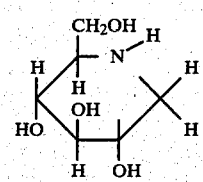

and was first extracted and isolated from a crude drug of the root skin of Morus alba (Yagi et al., Journal of Society of Japan, Agricultural Chemical 50, page 571, 1976 and Japanese Patent Application Laid-Open Specification No. 83951/77). We previously developed a process for preparing of the compound of the formula (III) from a microorganism belonging to the genus Streptomyces by the fermentation method (Japanese Patent Application Laid-Open Specification No. 84094/79).

The N-lower-alkyl derivative of moranoline of the structural formula is obtained by alkylation of the compound of the formula (III) (Japanese Patent Application Laid-Open Specification No. 12381/79). Applications of cyclodextrin glycosyltransferase are shown in various patent specifications and literature references. For example, the following techniques can be mentioned.

(a) Production of hesperetin dihydrochalcone-7-maltooligosides as sweetening agents (Amylase Symposidum, 4, page 61, 1972)

(b) Production of oligosaccharides having fructose units bonded to the terminals (Japanese Patent Application Laid-Open Specifications No. 20373/72 and No. 119092/79).

(c) Production of nojirimycin glucose oligomers (Japanese Patent Application Laid-Open Specification No. 23976/78)

(d) Production of cyclic dextrins (Japanese Patent Application Laid-Open Specification No. 88290/75)

(e) Production of α-glycosylstevioside as a sweetening agent (Japanese Patent Application Laid-Open Specification No. 5070/79)

These inventions utilize the following three characteristics possessed by cyclodectrin glycosyltransferase:

(1) Starch→cyclodextrin (cyclization)

(2) cyclodextrin+glucose→oligoglucose (coupling)

(3) (glucose)$_n$+(glucose)$_m$→(glucose)$_{n+x}$+(glucose)$_{m-x}$ (homologizing) in the above formula, m, n and x are integers (see Amylase Symposium, 7, page 61, 1972)

Recently, the substrate specificity of cyclodextrin glycosyltrasferase in the coupling reaction has recently been elucidated (see, for example, Agricultural and Biological Chemistry, 42, page 2369, 1978). The present invention is based on the novel finding that moranoline and N-lower-alkylmoranoline can be a substrate of cyclodextrin glycosyltransferase in the coupling reaction.

It has been revealed that moranoline and its derivatives are valuable as medicines for controlling increase of blood sugar lavels in sugar-loaded animals (Japanese Patent Application Laid-Open Specifications No. 83951/77, No. 12381/79 and No. 106477/79).

We made researches with a view to developing more valuable moranoline derivatives, and we have now completed the present invention.

Moranoline derivatives of the formula:

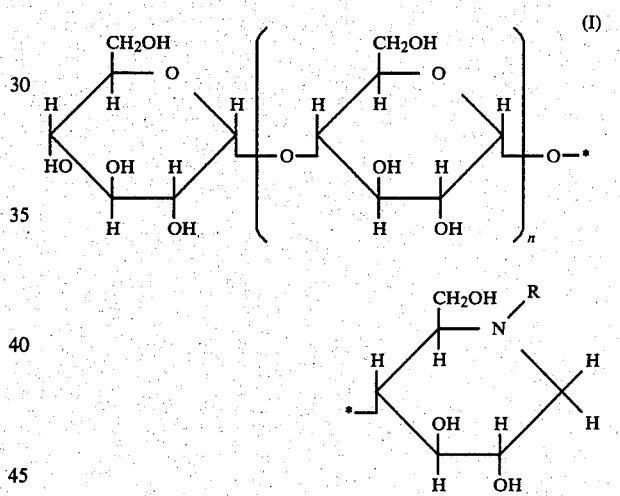

wherein n is an integer of from 0 to 7, and R stands for H or a lower alkyl group, are produced by reacting an aqueous solution containing a moranoline of the formula (II):

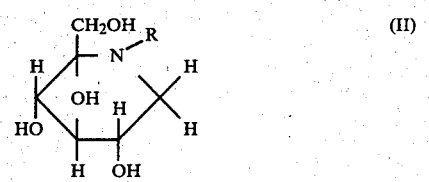

wherein R is as defined above and cyclodextrin or soluble starch with cyclodextrin glycosyltransferase to obtain a mixture containing a maranoline derivative of the formula (I) and isolating the mixture into respective components.

Glycosylmoranoline derivatives of the formula:

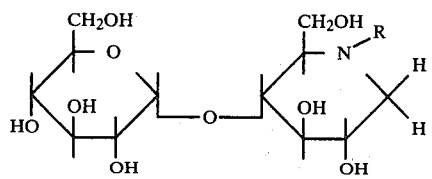

wherein R stands for hydrogen or a lower alkyl group, are produced by reacting a solution of a mixture containing a compound of the formula (I):

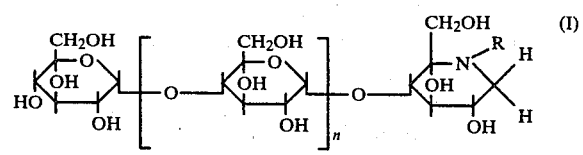

wherein R is as above defined and n is an integer of from 1 to 20, and a compound of the formula (IV):

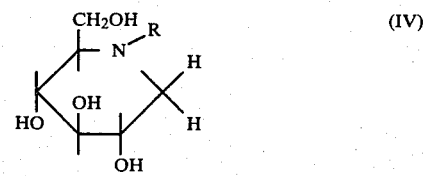

wherein R is as above defined, (with the proviso that the case where a compound of the formula (I) in which n is zero is used alone as the compound of the formula (I) is excluded) with α-1,4-glucanglucohydrolase directly or after addition of a cation exchange resin if necessary.

Cyclodextrin glycosyltransferase that is used in the present invention can be obtained by culturing a microorganism capable of producing this enzyme, for example, a microorganism belonging to the genus Bacillus or Klebsiella, in a nutrient medium containing a carbon source such as starch or bran, a nitrogen source such as corn steep liquor, polypeptone, corn gluten meal or yeast extract, an inorganic substance such as ammonium sulfate, calcium carbonate or magnesium chloride, and other substance suitable for production of the enzyme, and purifying the formed cyclodextrin glycosyltransferase by known purifying means such as salting-out, dialysis, adsorption on starch, desorption, gel filtration or ion exchange chromatography. A filtrate of the culture medium may be used as the crude enzyme liquid, but ordinarily, the enzyme is used in the form of a partially purified, highly purified or stabilized enzyme product.

If the compound (II) and cyclodextrin (starch or dextrin may be used instead) are reacted in the presence of the so obtained cyclodextrin glycosyltransferase, the intended product can be obtained. The reaction conditions are changed according to the origin of the cyclodextrin glycosyltransferase used, but ordinarily, the intended product is obtained by carrying out the reaction at a temperature of about 40° C. and a pH value of 5.0 to 8.5 for a reaction time of 1 to 3 days. Known separation and purification methods may be adopted for isolation of the intended product from the liquid reaction mixture. For example, the following procedures may be adopted.

At first, the liquid reaction mixture is passed through a column of a strongly acidic ion exchange resin to make basic substances adsorbed on the resin, and elution is carried out by using 0.5 N aqueous ammonia and the eluate is concentrated under reduced pressure. The concentrate is subjected to fractionation using a Sephadex column, and necessary fractions are collected and freeze-dried to obtain a white powder. Identification of the respective fractions can be accomplished by, for example, high-speed liquid chromatography. When the high speed liquid chromatography is carried out in a high speed liquid chromatograph (Model ALC/GPC-244 supplied by Waters Co.) by using a μ-Bondapak NH$_2$ column and performing development with acetonitrile/water (70/30) at a flow rate of 1.5 ml/min illustrated in Examples 2, 3 and 4 (FIGS. 1, 2 and 3), it is found that respective components have the following retention times.

TABLE 1

| Substance | Retention Time (minutes) |
|---|---|
| Moranoline | 4.3 |
| 4-(α-D-Glucosyl)-moranoline | 5.3 |
| 4-(α-D-Maltosyl)-moranoline | 6.6 |
| 4-(α-D-Maltotriosyl)-moranoline | 9.8 |
| 4-(α-D-Maltotetraosyl)-moranoline | 11.5 |
| N-methylmoranoline | 3.5 |
| 4-(α-D-glucosyl)-N-methylmoranoline | 4.1 |
| 4-(α-D-maltosyl)-N-methylmoranoline | 5.3 |
| 4-(α-D-maltotriosyl)-N-methylmoranoline | 6.9 |
| 4-(α-D-maltotetraosyl)-N-methylmoranoline | 9.1 |
| 4-(α-D-maltopentaosyl)-N-methylmoranoline | 11.9 |
| 4-(α-D-maltohexaosyl)-N-methylmoranoline | 15.2 |
| 4-(α-D-maltoheptaosyl)-N-methylmoranoline | 19.5 |
| 4-(α-D-maltooctanosyl)-N-methylmoranoline | 25.1 |
| N-ethylmoranoline | 3.3 |
| 4-(α-D-glucosyl)-N-ethylmoranoline | 3.9 |
| 4-(α-D-maltosyl)-N-ethylmoranoline | 5.1 |
| 4-(α-D-maltotriosyl)-N-ethylmoranoline | 6.8 |
| 4-(α-D-maltotetraosyl)-N-ethylmoranoline | 9.0 |
| 4-(α-D-maltopentaosyl)-N-ethylmoranoline | 12.1 |
| 4-(α-D-maltohexaosyl)-N-ethylmoranoline | 15.8 |
| 4-(α-D-maltoheptaosyl)-N-ethylmoranoline | 20.2 |
| N-propylmoranoline | 2.9 |
| 4-(α-D-glucosyl)-N-propylmoranoline | 3.5 |
| 4-(α-D-maltosyl)-N-propylmoranoline | 3.4 |
| 4-(α-D-maltotriosyl)-N-propylmoranoline | 5.7 |
| 4-(α-D-maltotetraosyl)-N-propylmoranoline | 7.6 |
| 4-(α-D-maltopentaosyl)-N-propylmoranoline | 10.1 |
| 4-(α-D-maltohexaosyl)-N-propylmoranoline | 13.2 |
| 4-(α-D-maltoheptaosyl)-N-propylmoranoline | 17.2 |
| 4-(α-D-maltooctanosyl)-N-propylmoranoline | 22.1 |

Elementary analysis values, molecular weights, specific rotation powers (aqueous solutions) and melting points of the intended products are as shown below. The molecular weights were measured by using a molecular weight measuring device, Hitachi Model 115. Parenthesized values are theoretical values or indicate concentrations at which specific rotation powers were measured.

TABLE 2

| Substance | Molecular Formula | Elementary Analysis Values (%) | | | Molecular Weight | $[\alpha]_D^{24}$ |
|---|---|---|---|---|---|---|
| | | C | H | N | | |
| 4-(α-D-gluco- | $C_{12}H_{23}O_9N \cdot \tfrac{1}{2}H_2O$ | 43.14 | 7.56 | 4.04 | 330 | 121.6° |

TABLE 2-continued

| Substance | Molecular Formula | C | H | N | Molecular Weight | $[\alpha]_D^{24}$ | Melting Point (° C.) |
|---|---|---|---|---|---|---|---|
| syl)-moranoline | | (43.10) | (7.24) | (4.19) | (325.31) | (1.0%) | |
| 4-(α-D-malto-syl)-moranoline | $C_{18}H_{33}O_{14}N \cdot H_2O$ | 42.63 (42.77) | 7.35 (6.98) | 2.94 (2.77) | 477 (487.45) | 143.9° (0.8%) | |
| 4-(α-D-maltotri-osyl)-moranoline | $C_{24}H_{43}O_{19}N \cdot 2H_2O$ | 42.44 (42.04) | 6.95 (6.91) | 2.28 (2.04) | 620 (649.59) | 161.9° (0.5%) | |
| 4-(α-D-maltotetra-osyl)-moranoline | $C_{30}H_{53}O_{24}N \cdot 2\tfrac{1}{2}H_2O$ | 41.97 (42.05) | 6.80 (6.82) | 1.99 (1.63) | 800 (811.73) | 167.1° (0.5%) | |
| 4-(α-D-glucosyl)-N-methylmoranoline | $C_{13}H_{25}O_9N \cdot 2H_2O$ | 41.67(%) (41.60) | 7.98(%) (7.79) | 3.93(%) (3.73) | 351 (339.34) | +95.2° (1.0%) | 124 ~127 |
| 4-(α-D-maltosyl)-N-methylmoranoline | $C_{19}H_{35}O_{14}N \cdot 2\tfrac{1}{2}H_2O$ | 41.67 (41.76) | 7.66 (7.38) | 2.73 (2.56) | 508 (501.48) | +130.45° (1.0%) | 153 ~155 |
| 4-(α-D-maltotriosyl)-N-methylmoranoline | $C_{25}H_{45}O_{19}N \cdot 2\tfrac{1}{2}H_2O$ | 42.64 (42.37) | 7.44 (7.11) | 2.06 (1.98) | 650 (663.62) | +152.02° (1.0%) | 174 ~176 |
| 4-(α-D-maltotetra-osyl)-N-methyl-moranoline | $C_{31}H_{55}O_{24}N \cdot 3H_2O$ | 42.01 (42.32) | 7.01 (6.99) | 1.87 (1.59) | 860 (825.76) | +155.98° (1.0%) | 190 ~194 |
| 4-(α-D-maltopenta-osyl)-N-methyl-moranoline | $C_{37}H_{65}O_{29}N \cdot 3H_2O$ | 42.39 (42.65) | 6.98 (6.87) | 1.60 (1.34) | 939 (987.91) | +163.14° (1.0%) | 204 ~208 |
| 4-(α-D-glucosyl)-N-ethylmoranoline | $C_{14}H_{27}O_{14}N \cdot 2H_2O$ | 45.44 (45.28) | 7.94 (7.87) | 3.93 (3.77) | 343 (353.37) | +76.2° (0.62%) | 122 ~126 |
| 4-(α-D-maltosyl)-N-ethylmoranoline | $C_{20}H_{37}O_{14}N \cdot 2H_2O$ | 43.51 (43.55) | 7.61 (7.49) | 2.61 (2.54) | 525 (515.51) | +116° (1.0%) | 138 ~143 |
| 4-(α-D-glucosyl)-N-propylmoranoline | $C_{15}H_{29}O_9N \cdot H_2O$ | 46.86 (46.75) | 8.19 (8.11) | 3.81 (3.63) | 358 (367.40) | +70.4° (1.0%) | 109 ~113 |

The so obtained intended products are novel substances which have not been introduced in any of literature references, and they have an excellent effect of controlling increase of blood sugar levels as shown below and they are valuable as medicines.

[Effect of Controlling Increase of Blood Sugar Levels]

Five-week-old male rats of the SD series are divided into groups, each consisting of 4 rats, and 2 g/Kg of sucrose and 5 mg/Kg of the test compound are orally administered. Blood is collected from the tail veins at predetermined intervals over a period of 180 minutes from the point of administration and the blood level values are measured. The area ($\Delta AUC$) below the time-blood level increase curve is determined. The blood level increase inhibition ratio of the test compound is calculated from the basal value obtained in the group to which water alone has been administered and the control value obtained in the group to which sucrose alone has been administered according to the following formula:

$$\text{inhibition ratio} = \frac{(\Delta AUC \text{ of control group}) - (\Delta AUC \text{ of test group})}{(\Delta AUC \text{ of control group}) - (\Delta AUC \text{ of basal group})} \times 100$$

The results of the above caculation of the blood level increase inhibition ratio are shown in the following Table.

TABLE 3

| Substance | Blood Level Increase Inhibition Ratio (%) |
|---|---|
| Moranoline | 19 |
| 4-(α-D-Glucosyl)-moranoline | 44 |
| 4-(α-D-Maltosyl)-moranoline | 35 |
| 4-(α-D-Maltotriosyl)-moranoline | 31 |
| 4-(α-D-Maltotetraosyl)-moranoline | 56 |
| 4-(α-D-glucosyl)-N-methylmoranoline | 56 |
| 4-(α-D-maltosyl)-N-methylmoranoline | 62 |

TABLE 3-continued

| Substance | Blood Level Increase Inhibition Ratio (%) |
|---|---|
| 4-(α-D-maltotriosyl)-N-methylmoranoline | 29 |
| 4-(α-D-maltotetraosyl)-N-methylmoranoline | 25 |
| 4-(α-D-maltopentaosyl)-N-methylmoranoline | 23 |
| 4-(α-D-glucosyl)-N-ethylmoranoline | 22 |
| 4-(α-D-maltosyl)-N-ethylmoranoline | 35 |
| 4-(α-D-glucosyl)-N-propylmoranoline | 24 |

With reference to compounds (I) where n=0, we have made another research and found that, by very simple means of reacting a mixed solution obtained in accordance with a method of claim 2 with α-1,4-glucan-glucohydrolase (E.C.-3,2,1,3α-1,4-Glucanglucohydrolase), oligoglucosylmoranoline or N-lower-alkyl-moranoline in which n is 1 or a larger integer can be converted in a very good yield to 4-(α-D-glucosyl)-moranoline or 4-(α-D-glucosyl)-N-lower-alkylmoranoline in which n is zero.

α-1,4-Glucanglucohydrolase that is used in the above route is mainly produced by moulds such as *Rhizopus niveus, Rhizopus delemar, Aspergillus niger* and *Aspergillus awamori*, and it also is called glucoamylase, amyloglucosidase, γ-amylase or taka-amylase B.

In carrying out this method, this enzyme may be used in the form of an enzyme crystal or a culture medium containing this enzyme, for example, a crude enzyme liquid obtained by culturing *Rhizopus niveus*. Furthermore, other carbohydrate-decomposing enzyme such as α-amylase or β-amylase may be present in the enzyme to be used in the present invention. The action of α-1,4-glucanglucohydrolase is an action of decomposing starch from non-reducing terminals into glucose units. Of course, maltose, maltotriose, maltotetraose and higher oligosaccharides of α-1,4 linkages can similarly be decomposed to glucose units by the present enzyme. These reactions may be represented as follows:

Starch + nH₂O → n.glucose
G-G-G ... —G + mH₂O → mG wherein n and m are integers, G stands for glucose, and G-G indicates an α-1,4 linkage. Incidentally, as will be obvious to those skilled in the art, the origin of the enzyme that is used in the present method is not limited to moulds.

The first characteristic feature of the present method resides in the finding of the heretofore unknown fact that while maltose having the formula

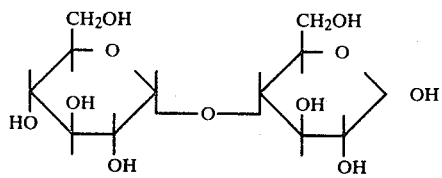

is promptly decomposed to glucose by α-1,4-glucan-glucohydrolase, 4-(α-D-glucosyl)-moranoline and 4-(α-D-glucosyl)-N-lower-alkylmoranoline are hardly decomposed by α-1,4-glucanglucohydrolase and oligoglucosylmoranolines and N-lower-alkyloligoglucosylmoranolines of the structural formula (I), except those in which n is zero, are decomposed by this enzyme at a speed which is not higher than the maltose-decomposing speed but is practically sufficiently high.

This point will now be described in detail.

The reaction of the present invention is generally expressed as follows:

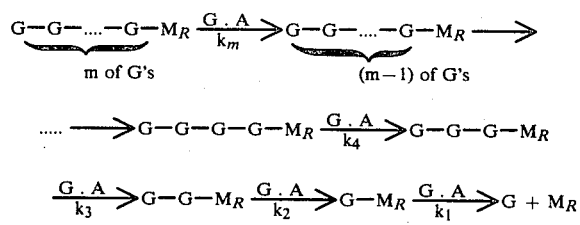

wherein G stands for glucose, $M_R$ stands for moranoline or N-lower-alkylmoranoline, m is an integer, G.A stands for α-1,4-glucanglucohydrolase, each bondage indicates an α-1,4 linkage, and stand for rate constants of reactions of the respective stages.

Practically, reactions of the respective stages are advanced on a mixture of compounds differing in the glucose number (m). Accordingly, in order to accumulate intended G-$M_R$ in the liquid reaction mixture, it is indispensable that rate constants should be sufficiently high but the rate constant k1 should be sufficiently low. FIG. 4 clarifies this point. FIG. 4 will now be explained. A predetermined amount of N-methyloligoglycosyl-moranoline is adsorbed on 1 g of Dowex 50W×2 (H+) in an Erlenmeyer flask having a capacity of 125 ml, and they are suspended in 50 ml of distilled water and 10 mg of α-1,4-glucanglucohydrolase is added to the suspension. Incubation is carried out at 40° C., and 500 μl of the liquid is sampled at predetermined intervals and the amount of glucose is determined. When maltose is used as the substrate, it is mixed with 1 g of Dowex 50W×2 (H+) and in this state, incubation is carried out at 40° C.

Determination of Glucose 1 ml of 0.3 N Ba(OH)$_2$ and 1 ml of 5% ZnSO$_4$ are added to 500 μl of the reaction mixture liquid and centifugal separation is carried out under a load of 2000 g for 10 minutes. 30 μl of the supernatant is taken and 3 ml of a commercially available glucose color reagent (manufactured by Boehunger Mannheim Co.; new blood sugar test) is added to the sampled supernatant. The mixture is sufficiently stirred and allowed to stand at room temperature for 35 minutes and the absorbance at 420 nm is measured. Separately, a glucose reference reagent (9.1 mg/dl) is similarly treated and the absorbance at 420 nm is measured. Based on these measurements, the amount of glucose formed in the reaction mixture liquid is determined.

Enzyme

About 22 units/mg of α-1,4-glucanglucohydrolase (crystal) derived from *Rhizopus niveus* (supplied by Seikagaku Kogyo K.K.)

Activity of Enzyme 1 ml of the enzyme solution is mixed with 5 ml of a 1.0% starch solution and 4 ml of a 0.05 M acetate buffer solution, and incubation is carried out at 40° C. and the amount of the formed reduced sugar (glucose) is determined according to the Fehling-Lehman-Schoorl method.

One unit of the enzyme corresponds to the activity of forming 10 mg of glucose for 30 minutes.

Substrate and Amount of Substrate Adsorbed on Resin:

| | |
|---|---|
| maltose | 100 mg |
| 4-(α-D-glucosyl)-N-methylmoranoline | 100 mg |
| 4-(α-D-maltosyl)-N-methylmoranoline | 50 mg |
| 4-(α-D-maltotriosyl)-N-methylmoranoline | 50 mg |
| 4-(α-D-maltotetraosyl)-N-methylmoranoline | 50 mg |

The experimental results are shown in FIG. 4. The reaction time is plotted on the abscissa and the ratio of decomposition based on complete decomposition of glucose is plotted on the ordinate. Since decomposition of N-methylglucosylmoranoline is extremely small as shown in FIG. 4, in case of N-methyloligoglucosyl-moranolines, in order to compare the decomposition speed with that of maltose each value is expressed as a relative value calculated on the supposition that the value obtained when decomposition proceeds to glucosylmoranoline or N-methylglucosylmoranoline is 100%. After determination of the amount of glucose, the reaction liquid is filtered and the ion exchange resin (Dowex 50W×2) is collected, washed with water sufficiently and eluted with 0.5 N aqueous ammonia. The eluate is concentrated under reduced pressure and dried to the solid. The solid is dissolved in distilled water and subjected to high speed liquid chromatography (Model ALC/GPC-244 supplied by Waters Co., μ-Bondapak NH$_2$ column, acetonitrile/water=70/30, 1.5 cc/min), and the reaction product is identified by a chromatopac Model C-R1A supplied by Shimadzu Seisakusho K. K. The ratios of formation of N-methylmoranoline are about 3%, about 2%, about 2%, about 1% and about 2% in case of 4-(α-D-glucosyl)-N-methylmoranoline, 4-(α-D-amltosyl)-N-methylmoranoline, 4-(α-D-maltotriosyl)-N-methylmoranoline and 4-(α-D-maltotetraosyl)-N-methylmoranoline, respectively. A similar tendency is observed in oligoglucosylmoranolines. In this case, the speed of the enzymatic reaction is higher than in N-methyloligosylmoranolines, and under the same reaction conditions as adopted for N-methyloligoglucosylmoranolines, maltose is decomposed substantially completely in 1 hour but the decomposition ratios 4-(α-D-glucosyl)-moranoline, 4-(α-D-maltosyl)-moranoline and 4-(α-D-maltotriosyl)-moranoline are about 3%, about 53% and about 50%, respectively (the meaning of the decomposition ratio is the same as described above with respect to N-methyloligoglycosylmoranolines). In the foregoing experiments, the substrate is adsorbed on a strongly acidic ion exchange resin, Dowex 50W×2 (maltose is mixed with the resin). The reason for the use of this resin will be described hereinafter in detail. The presence of an excessive amount of the strongly acidic ion exchange resin inhibits the enzymatic reaction. However, no substantial problem arises if the amount of the resin is up to about 4 g in 100 ml of the reaction liquid. If the resin is saturated with moranoline, N-lower-alkylmoranolines, oligoglycosylmoranolines and N-lower-alkylmoranolines, the reaction is not inhibited even when the resin is further added.

Ordinarily, α-1,4-glucanglucohydrolase is used in a buffer solution, but even if the reaction is carried out in distilled water, although the activity is reduced to some extent, no practical disadvantage is caused.

The second characteristic feature of the present method resides in the finding that if the above-mentioned mixture is adsorbed on a cation exchange resin and is reacted with α-1,4-glucanglucohydrolase, the mixture concentration in the reaction liquid can remarkably be increased, and the reaction is not influenced by the state of the mixture and the product inhibition by moranoline or N-lower-alkylmoranoline formed in a minute amount is not caused, resulting in great industrial advantages. This point will now be described in detail.

Moranoline, N-lower-alkylmoranolines, oligoglycosylmoranolines and N-lower-alkyloligoglucosylmoranolines inhibit the activity of α-1,4-glucanglucohydrolase. The intensities of inhibition of these compounds are shown in Table 4. The inhibition is determined according to the following method.

Enzyme

Glucoamylase (crystal) derived from *Rhizopus nivens* (supplied by Seikagaku Kogyo K. K.) is dissolved in distilled water so that the concentration is 50 μg/ml and the enzyme is used in the form of the so obtained solution.

Substrate

Soluble starch is dissolved in a buffer solution at a high temperature so that the concentration is 1.4%, and the solution is cooled to room temperature and used.

Buffer Solution 0.1 M phosphate buffer solution (pH=5.7)

Starting Liquid

|  | Blank (I) | Blank (II) | Control | Test Sample |
|---|---|---|---|---|
| Enzyme | — | — | 150 μl | 150 μl |
| Substrate | 250 μl | 250 μl | 250 μl | 250 μl |
| Inhibitor | 100 μl | — | — | 100 μl |
| Distilled Water | 150 μl | 250 μl | 100 μl | — |

Procedures

The starting liquid is incubated at 40° C. for 10 minutes, and 1 ml of a 0.3 N solution of Ba(OH)$_2$ and 1 ml of a 5% solution of ZnSO$_4$ are added. Centifugal separation is conducted under a load of 2000×g for 10 minutes, and 30 μl of the supernatant is sampled and 3 ml of a glucose color reagent (supplied by Boelunger Mannheim Co.; new blood sugar test) was added to the supernatant. The mixture was allowed to stand at room temperature for 35 minutes and the absorbance at 420 nm is measured. The percent inhibition is calculated according to the following formula:

$$\text{Percent Inhibition} = \frac{(C - B) - (T - B')}{(C - B)} \times 100$$

wherein C stands for the absorbance of the control, T stands for the absorbance of the test sample, B' stands for the absorbance of the blank (I), and B stands for the absorbance of the blank (II).

The percent inhibition is also determined in respect of dilutions, and the concentration (IC$_{50}$) providing 50% inhibition is found. In Table 4, the percent inhibition obtained at a parenthesized concentration is shown when the inhibition is low.

TABLE 4

|  | IC$_{50}$(μg/ml) |
|---|---|
| moranoline | 9.3 |
| 4-(α-D-glucosyl)-moranoline | 15% (>200 μg/ml) |
| 4-(α-D-maltosyl)-moranoline | 0% (>200 μg/ml) |
| 4-(α-D-maltotriosyl)-moranoline | 0% (>200 μg/ml) |
| 4-(α-D-maltotetraosyl)-moranoline | 0% (>200 μg/ml) |
| M-methylmoranoline | 1.6 |
| 4-(α-D-glucosyl)-N-methylmoranoline | 125 |
| 4-(α-D-maltosyl)-N-methylmoranoline | 1150 |
| 4-(α-D-maltotriosyl)-N-methylmoranoline | 160 |
| 4-(α-D-maltotetraosyl)-N-methylmoranoline | 180 |
| 4-(α-D-maltopentaosyl)-N-methylmoranoline | 120 |
| N-ethylmoranoline | 6.9 |
| 4-(α-D-glucosyl)-N-ethylmoranoline | 38% (>800 μg/ml) |
| N-propylmoranoline | 56 |

As is seen from Table 4, the inhibition of moranoline and N-lower-alkylmoranolines is very strong, and the inhibition is ordinarily reduced by glycosylation. Accordingly, the reaction is advanced at a low concentration, but at a concentration of scores to several hundreds of μg/ml, the reaction is substantially inhibited. As is seen from Table 4, this critical concentration differs according to the mixing ratio of the respective components in the mixture and the kind of the lower alkyl group. Since the inhibition of moranoline and N-lower-alkylmoranolines is several hundred to several thousand times as high as that of glycosylated substances, the critical concentration is extremely varied by the amounts of moranoline and lower-alkyl-moranolines contained. In the actual operation, however, a higher concentration is preferred from the viewpoint of the manufacturing cost, and the reaction should not be influenced by the state of the mixture. We made researched while taking this point into account, and found that when the enzyme is used in the state where it is adsorbed on an acidic cation exchange resin, the reaction is advanced at a concentration higher than several thousand μg/ml and the reaction is not influenced by the state of the mixture. We have now completed the present invention based on the finding of this novel fact. Incidentally, in Examples 6,7,8 and 10 given hereinafter, the reaction was not advanced at all if the enzyme was used in the state where it was not adsorbed on a strongly acidic cation exchange resin.

The present invention will now be described in detail with reference to the following Examples.

EXAMPLE 1

(A) Culturing of *Bacillus macerans*

(1) A 500 ml capacity Erlenmeyer flask was charged with 150 ml of a culture medium comprising 1% of corn steep liquor, 1% of soluble starch, 0.5% of $(NH_4)_2SO_4$ and 0.5% of $CaCO_3$ and having a pH value of 7, and the culture medium was sterilized at 120° C. for 15 minutes. Then 4 platinum spoonfuls of cells of *Bacillus macerans* IFO 3490, which had been sufficiently propagated on a slant culture medium comprising 1% of peptone, 0.5% of yeast extract, 0.3% of glucose, 1.5% of glycerol, 0.3% of NaCl, 1.5% of neutralized liver digest (OXOID ®) and 1.5% of agar were inoculated on the above culture medium, and culturing was conducted at 37° C. for 3 days. Then, 300 ml of the culture medium was inoculated on 9 l of a culture medium having the same composition in a jar fermentator. Culturing was conducted at 37° C. for 3 days under sufficient aeration and stirring, whereby an enzyme liquid containing 130 to 150 units of the enzyme (the definition of the unit will be described hereinafter) was obtained in the form of a supernatant after centrifugal separation.

(2) A culture medium comprising 4% of wheat bran, 0.5% of corn steep liquor, 0.5% of soluble starch, 0.5% of $(NH_4)_2SO_4$ and 0.5% of $CaCO_3$ and having a pH value of 6.7 was sterilized at 120° C. for 15 minutes and 200 ml of the sterilized culture medium was charged in an Erlenmeyer flask having a capacity of 500 ml. The culture medium was inoculated with 3 platinum spoonful of cells of *Bacillus macerans* IFO 3490, and shaking culturing was conducted at 37° C. for 4 days to obtain an enzyme liquid containing about 90 units of the enzyme in the form of a supernatant after centrifugal separation.

(B) Unit of activity of cyclodextrin glycosyltransferase

Soluble starch (for biochemical assay; supplied by Nakarai Kagaku K.K.) was dissolved at a concentration of 0.7% in a 0.05 M acetate buffer solution having a pH value of 5.5 to form a substrate solution. 50 μl of the enzyme liquid was added to 950 μl of the so formed substrate solution, and the reaction was conducted at 40° C. for 10 minutes. The reaction was stopped by addition of 0.5 ml of 0.5 N acetic acid. 100 μl of the reaction liquid was taken and mixed with 3 ml of water and 0.8 μl of an iodine solution formed by dissolving iodine into a 0.25 M KI solution so that the iodine concentration was 0.01 M. The mixture was stirred and the absorbance ($A_t$) at 660 nm was measured.

Separately, 50 μl of water and 0.5 ml of 0.5 N acetic acid were added to 950 μl of the substrate solution described above, and 100 μl of the so formed solution was taken and mixed with the iodine solution in the same manner as described above. The absorbance ($A_r$) at 660 nm was measured. One unit of the enzyme is defined by the following formula:

$$1 \text{ unit} = \frac{A_r - A_t}{A_r} \times 100 \times 2$$

This value corresponds to the activity of 1 ml of the enzyme solution for decreasing the absorbance by 1% by the reaction at 40° C. for 1 minute.

(C) Preparation of crude enzyme solution

The culture medium obtained by culturing of *Bacillus macerans* IFO 3490 was subjected to centrifugal separation and the supernatant was recovered. The supernatant was freeze-dried and dissolved in a small amount of water to obtain an enzyme concentrate. Dialysis was carried out sufficiently at 5° C. by using water as the external liquid from which low molecules had been removed was used as the crude enzyme solution.

(D) Reaction

In 400 ml of the crude enzyme solution having an activity of 870 units (348000 units as a whole) were dissolved 8 g of moranoline hydrochloride and 8 g of α-cyclodextrin, and shaking culturing was conducted at 38° C. and a pH value of 5.7 for 3 days. A part of the reaction liquid was taken and the basic substances were collected therefrom, and analysis was conducted by using a high speed liquid chromatograph (ALC/GPC-244 manufactured by Waters Co., saccharide analysis column (μ-Bondapak CH), acetonitrile/water (70/30), developing rate of 1.5 ml/min). The area ratios of the respective fractions on the differential refractometer were determined by using Chromatopac C-R1A manufactured by Shimadzu Seisakusho to obtain the following results:

| | |
|---|---|
| unreacted moranoline | 43% |
| 4-(α-glucosyl)-moranoline | 16% |
| 4-(α-D-maltosyl)-moranoline | 16% |
| 4-(α-D-maltotriosyl)-moranoline | 12% |
| 4-(α-D-maltotetraosyl)-moranoline | 8% |

(E) Isolation and purification

About 400 ml of the reaction liquid was heated at 120° C. for 10 minutes, and 160 ml of trichloroethylene was added thereto and the mixture was violently stirred. The lower layer was thrown away. The upper layer was subjected to centrifugal separation to obtain a transparent supernatant. The supernatant was passed through a column packed with 80 ml of a strongly acidic ion exchange resin (Dowex 50W×2, H+type) to make the basic substances adsorbed on the column. Elution was carried out by using 0.5 N aqueous ammonia and the eluate was freeze-dried. The obtained powder was treated with Sephadex G-15 (48 mm in diameter and 850 mm in height), Sephadex G-25 (55 mm in diameter and 470 mm in height) and Sephadex G-10 (40 mm in diameter and 820 mm in height) while the respective fractions were identified by a high speed liquid chromatograph (ALC/GPC 244 manufactured by Waters Co., μ-Bondapak CH column, acetonitrile/water of 70/30, 1.5 ml/min), to obtain the intended oligoglycosylmoranolines.

EXAMPLE 2

5 g of N-methylmoranoline was dissolved in a small amount of water and the pH value was adjusted to 5.68 by 3 N hydrochloric acid (the volume of the solution was 25 ml after the adjustment of the pH value).

80 g of α-cyclodextrin was dissolved in 3975 ml of the crude enzyme solution having an activity of 250 units/ml, and the aqueous solution of N-methylmoranoline was added and the pH value was readjusted to 5.68. Shaking culture was conducted at 39° C. for 3 days to effect reaction. The reaction liquid was subjected to centrifugal separation, and the supernatant was passed through a column of Dowex 50W×2 (H+) (the amount of the resin was 100 ml) to make basic substances adsorbed on the resin. Elution was carried out by using 0.5 N aqueous ammonia and the eluate was concentrated under reduced pressure and dried to the solid (cf. FIG. 1). The obtained powder was dissolved in a small amount of water, and the solution was passed through a column of Sephadex G-15 (48 mm in diameter and 850 mm in length), and fractions, each having a volume of 5 ml, were recovered and identified by a liquid chromatograph Model ALC/GPC-244 using a μ-Bondapak NH$_2$ column (acetonitrile/water=70/30; 1.5 ml/min). The intended fractions were collected, concentrated under reduced pressure and freeze-dried to obtain intended oligoglycosyl-N-methylmoranoline.

EXAMPLE 3

500 mg of N-ethylmoranoline was dissolved in a small amount of water and the pH value was adjusted to 5.8 by 1 N hydrochloric acid (the volume of the solution after the adjustment of the pH value was 20 ml).

Separately, 8 g of α-cyclodextrin was dissolved in 380 ml of the crude enzyme liquid having an activity of 260 units/ml. Both the solutions were mixed, and the pH value was readjusted to 5.77. Shaking culture was conducted at 39° C. for 3 days to effect reaction. Oligoglycosyl-N-ethylmoranoline was recovered from the reaction liquid in the same manner as described in Example 2.

EXAMPLE 4

500 ml of N-propylmoranoline was dissolved in a small amount of water and the pH value was adjusted to 5.7 by 1 N hydrochloric acid (the volume of the solution was 20 mg after the adjustment of the pH value).

Separately, 8 g of α-cyclodextrin was dissolved in 380 ml of the crude enzyme liquid having an activity of 260 units/ml. Both the solutions were mixed and the pH value was readjusted to 5.7. Shaking culture was conducted at 39° C. for 3 days and oligoglycosyl-N-propylmoranoline was recovered from the reaction liquid in the same manner as described in Example 2.

EXAMPLE 5

6.5 of moranoline was dissolved in a small amount of water and the pH value was adjusted to 5.7 by 3 N hydrochloric acid (the volume of the solution was 32.5 ml after the adjustment of the pH value).

26 g of α-cyclodextrin was dissolved in 1300 ml of the crude enzyme solution of cyclodextrin glycosyltransferase having an activity of 460 units/ml, and the aqueous solution of moranoline was added and the pH value was readjusted to 5.67. The reaction mixture was shaked at 39° C. for 3 days.

The reaction liquid was subjected to centrifugal separation, and the supernatant was passed through a column of Dowex 50W×2 (H+) (the amount of the resin was 50 ml) to make basic substances adsorbed on the resin. Elution of a part (about 2 ml) of the resin washed sufficiently with water was carried out by using 0.5 N aqueous ammonia and the eluate was concentrated under reduced pressure and dried to the solid. The obtained powder was dissolved in a small amount of water, and the solution was analyzed by a chromatopac (Model C-R1A manufactured by Shimadzu Seisakusho K.K.) after high speed liquid chromatography by using a chromatograph Model ALC/GPC-244 supplied by Waters Co. (μ-Bondapak NH$_2$ column, acetonitrile/water=70/30, 1.5 ml/min) (the composition of the mixture before reaction with α-1,4-glucanglucohydrolase was thus determined). Then, about 48 ml of the remaining resin was suspended in 1200 ml of water and 120 mg (about 22 units/mg) of α-1,4-glucanglucohydrolase derived from *Rhizopus niveus* was added. Incubation was carried out at 40° C., and the reaction mixture was sampled at predetermined intervals and the amount of glucose formed in the reaction mixture was determined to trace the state of advance of the reaction. The amount of glucose was abruptly increased after the start of the reaction and the reaction ratio was elevated to 89% in 5 hours. The reaction was further conducted and was stopped at the point of 25 hours from the start of the reaction. The resin was recovered by filtration, washed sufficiently with water and eluated with 0.5 N aqueous ammonia, and the eluate was concentrated under reduced pressure and dried to the solid. The obtained powder was subjected to high speed liquid chromatography in the same manner as described above, and the mixture after the reaction was analyzed by the chromatopac. The obtained results were as shown below.

|  | before reaction | after reaction |
| --- | --- | --- |
| moranoline | 25.1% | 31.7% |
| 4-(α-D-glucosyl)-moranoline | 31.0% | 68.3% |
| 4-(α-D-maltosyl)-moranoline | 17.2% | 0% |
| 4-(α-D-maltotriosyl)-moranoline | 11.2% | 0% |
| 4-(α-D-maltotetraosyl)-moranoline | 7.8% | 0% |
| 4-(α-D-maltopentaosyl)-moranoline | 4.9% | 0% |
| 4-(α-D-maltohexaosyl)-moranoline | 2.0% | 0% |
| 4-(α-D-maltoheptaosyl)-moranoline | 0.5% | 0% |
| 4-(α-D-maltooctanosyl)-moranoline | 0.3% | 0% |

EXAMPLE 6

2 g of a mixture shown in FIG. 5 was adsorbed on 10 ml of Dowex 50W×2 (H+) and the resin was suspended in 500 ml of water, and 50 mg (about 22 units/mg) of α-1,4-glucanglucohydrolase was added to the suspension. Reaction was conducted at 40° C. for 17 hours, and the reaction liquid was filtered to collect the resin. The resin was eluted with 0.5 N aqueous ammonia and the eluate was concentrated under reduced pressure and dried to the solid. The recovered solid was subjected to high speed liquid chromatography by using a liquid chromatograph, Model ALC/GPC-244 (supplied by Waters Co.,) and was analyzed by a chromatopac (Model C-R1A supplied by Shimadzu Seisakusho K.K.) to obtain results shown in FIG. 6. The mixing ratios of the respective components in FIGS. 5 and 6 were as shown below.

| | Symbol in Drawings | Before Reaction (FIG. 5) | After Reaction (FIG. 6) |
|---|---|---|---|
| moranoline | A | 4.6% | 5.3% |
| 4-(α-D-glucosyl)-moranoline | B | 13.2% | 91.5% |
| 4-(α-D-maltosyl)-moranoline | C | 14.0% | 3.0% |
| 4-(α-D-maltotriosyl)-moranoline | D | 14.9% | 0% |
| 4-(α-D-maltotetraosyl)-moranoline | E | 13.2% | 0% |
| 4-(α-D-maltopentaosyl)-moranoline | F | 13.5% | 0% |
| 4-(α-D-maltohexaosyl)-moranoline | G | 11.0% | 0% |
| 4-(α-D-maltoheptaosyl)-moranoline | H | 9.0% | 0% |
| 4-(α-D-maltooctanosyl)-moranoline | I | 4.0% | 0% |

EXAMPLE 7

Under the same conditions as described in Example 6, the reaction was carried out at 40° C. for 26 hours. A mixture of 5.8% of moranoline and 93.2% of 4-(α-D-glucosyl)-moranoline was obtained. The presence of other components was not detected.

EXAMPLE 8

200 mg of the mixture shown in FIG. 5 was dissolved in 4 l of water, and the pH value was adjusted to 5.7 by 0.5 N HCl and 200 mg (about 22 units/mg) of α-1,4-glucanglucohydrolase was added to the solution. Reaction was carried out at 40° C. for 41 hours, and the reaction liquid was passed through a column of 10 ml of Dowex 50W×2 (H+). The resin was washed with water sufficiently and eluted with 0.5 N aqueous ammonia. The eluate was concentrated under reduced pressure and dried to the solid. The obtained powder was dissolved in a small amount of water and the high speed liquid chromatography was carried out under the same conditions as described in Example 1. It was found that the product was a mixture of 6% of moranoline and 93.4% of 4-(α-D-glucosyl)-moranoline. The presence of other components was not detected.

EXAMPLE 9

1 g of N-methylmoranoline was dissolved in a small amount of water, and the pH value was adjusted to 5.7 by 1 N hydrochloric acid (the volume after the adjustment of the pH value was 10 ml). Separately, 16 g of α-cyclodextrin was added to 790 ml of a crude enzyme liquid of cyclodextrin glycosyltransferase (336 units/ml). Both the liquids were mixed together, and the pH value was readjusted to 5.6. Reaction was carried out at 39° C. for 2 days under shaking. The reaction liquid was subjected to centrifugal separation, and the supernatant was passed through a column of Dowex 50W×2 (H+) (the amount of the resin was 8 ml) to make basic substances adsorbed on the resin. The resin was washed with water sufficiently, and a part (about 2 ml) of the resin was sampled and was concentrated under reduced pressure and dried to the solid, and under the same conditions as described in Example 5, the obtained powder was subjected to the liquid chromatography and analyzed by the chromatopac (the composition of the mixture before the reaction with α-1,4-glucanglucohydrolase was thus determined). About 6 ml of the remaining resin was suspended in 150 ml of water, and 90 mg (about 22 units/mg) of α-1,4-glucanglucohydrolase was added to the suspension and the reaction was carried out at 40° C. for 48 hours. The reaction liquid was filtered to collect the resin, and the resin was washed with water sufficiently and eluted with 0.5 N aqueous ammonia. The eluate was concentrated under reduced pressure and dried to the solid. The obtained powder was subjected to the liquid chromatography and analyzed by the chromatopac.

The obtained results were as shown below.

| | Before Reaction | After Reaction |
|---|---|---|
| N-methylmoranoline | 19.0% | 21.3% |
| 4-(α-D-glucosyl)-N-methylmoranoline | 11.9% | 61.7% |
| 4-(α-D-maltosyl)-N-methylmoranoline | 13.3% | 15.4% |
| 4-(α-D-maltotriosyl)-N-methylmoranoline | 13.1% | 1.6% |
| 4-(α-D-maltotetraosyl)-N-methylmoranoline | 11.9% | 0% |
| 4-(α-D-maltopentaosyl)-N-methylmoranoline | 10.9% | 0% |
| 4-(α-D-maltohexaosyl)-N-methylmoranoline | 10.4% | 0% |
| 4-(α-D-maltoheptaosyl)-N-methylmoranoline | 8.1% | 0% |

EXAMPLE 10

1 g of N-propylmoranoline was dissolved in a small amount of water, and the pH value was adjusted to 5.7 by 1 N hydrochloric acid (the volume after the adjustment of the pH value was 20 ml). Separately, 16 g of α-cyclodextrin was added to 790 ml of a crude enzyme liquid of cyclodextrin glycosyltransferase (260 units/ml). Both the liquids were mixed together, and the pH value was readjusted to 5.7. Reaction was carried out at 39° C. for 2 days under shaking. The reaction liquid was subjected to centrifugal separation, and the supernatant was passed through a column of Dowex 50W×2 (H+) (the amount of the resin was 8 ml) to make basic substances adsorbed on the resin. The resin was washed with water sufficiently, and a part (about 2 ml) of the resin was sampled and was concentrated under reduced pressure and dried to the solid, and under same conditions as described in Example 5, the obtained powder was subjected to the liquid chromatography and analyzed by the chromatopac (the composition of the mixture before the reaction with α-1,4-glucanglucohydrolase was thus determined). About 6 ml of the remaining resin was suspended in 150 ml of water, and 15 mg (about 22 units/mg) of α-1,4-glucanglucohydrolase was added to the suspension and the reaction was carried out at 40° C. for 26 hours. The reaction liquid was filtered to collect the resin, and the resin was washed with water sufficiently and eluted with 0.5 N aqueous ammonia. The eluate was concentrated under reduced pressure and dried to the solid. The obtained powder was subjected to the liquid chromatography and analyzed by the chromatopac.

The obtained results were as shown below.

| | Before Reaction | After Reaction |
|---|---|---|
| N-propylmoranoline | 19.5% | 24.2% |
| 4-(α-D-glucosyl)-N-propylmoranoline | 16.7% | 75.1% |
| 4-(α-D-maltosyl)-N-propylmoranoline | 10.2% | 0% |
| 4-(α-D-maltotriosyl)-N-propylmora- | 10.0% | 0% |

| | Before Reaction | After Reaction |
|---|---|---|
| noline | | |
| 4-(α-D-maltotetraosyl)-N-propyl-moranoline | 10.3% | 0% |
| 4-(α-D-maltopentaosyl)-N-propyl-moranoline | 9.8% | 0% |
| 4-(α-D-maltohexaosyl)-N-propyl-moranoline | 8.3% | 0% |
| 4-(α-D-maltoheptaosyl)-N-propyl-moranoline | 7.8% | 0% |
| 4-(α-D-maltooctanosyl)-N-propyl-moranoline | 5.6% | 0% |

BRIEF DESCRIPTION OF THE DRAWINGS

In FIGS. 5 and 6, the differential refraction is plotted on the ordinate and the development time is plotted on the abscissa, and numerical figures indicate retention times (minutes), S represents the solvent and A, B, C, D, E, F, G, H and I show oligoglycosyl-moranolines.

Figure 1:
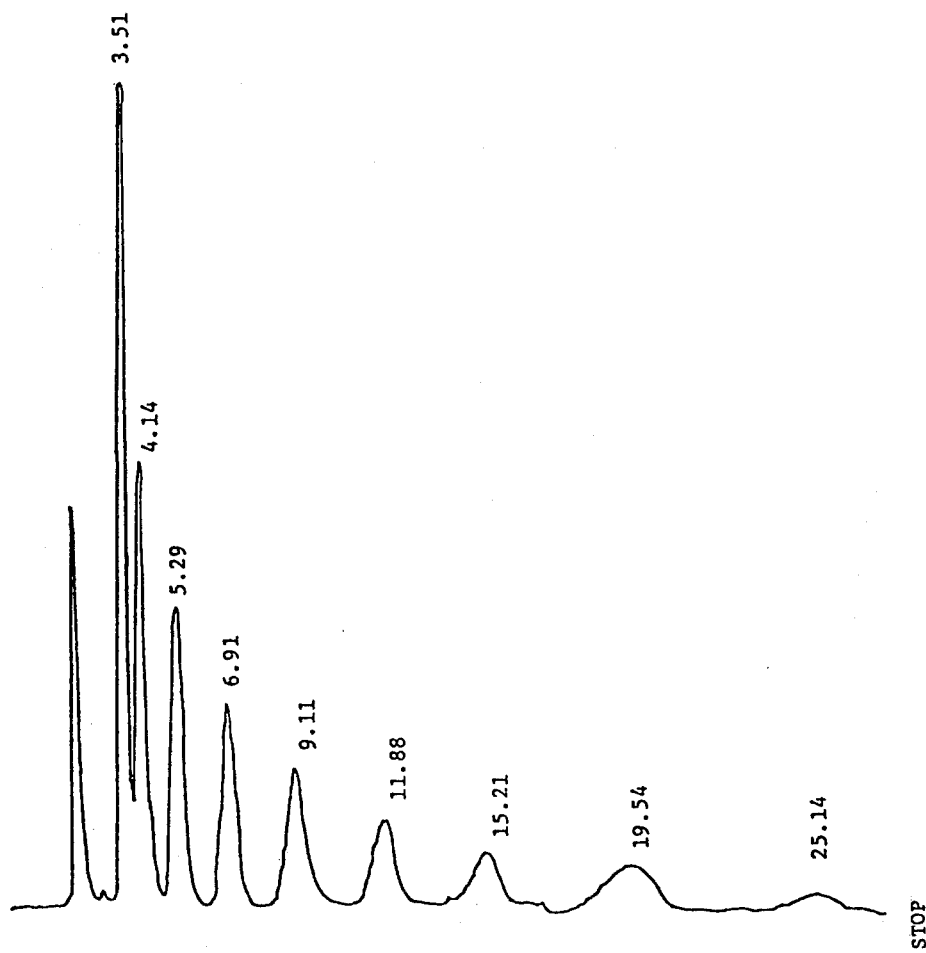
FIGS. 1, 2 and 3 show results of the high speed liquid chromatography (Model ALC/GPC-244 supplied by Waters Co.) of the basic fractions obtained in Examples 2, 3 and 4, respectively. A μ-Bondapak NH$_2$ column was used and development was conducted with acetobitrile/water (70/30), and analysis was carried out by using a chromatopac C-R2A manufactured by Shimadzu Seisakusho. In each FIG., the differential refraction index is plotted on the ordinate and the developing time is plotted on the abscissa. Numerical figures in the drawings indicate the retention times (minutes).
Figure 2:
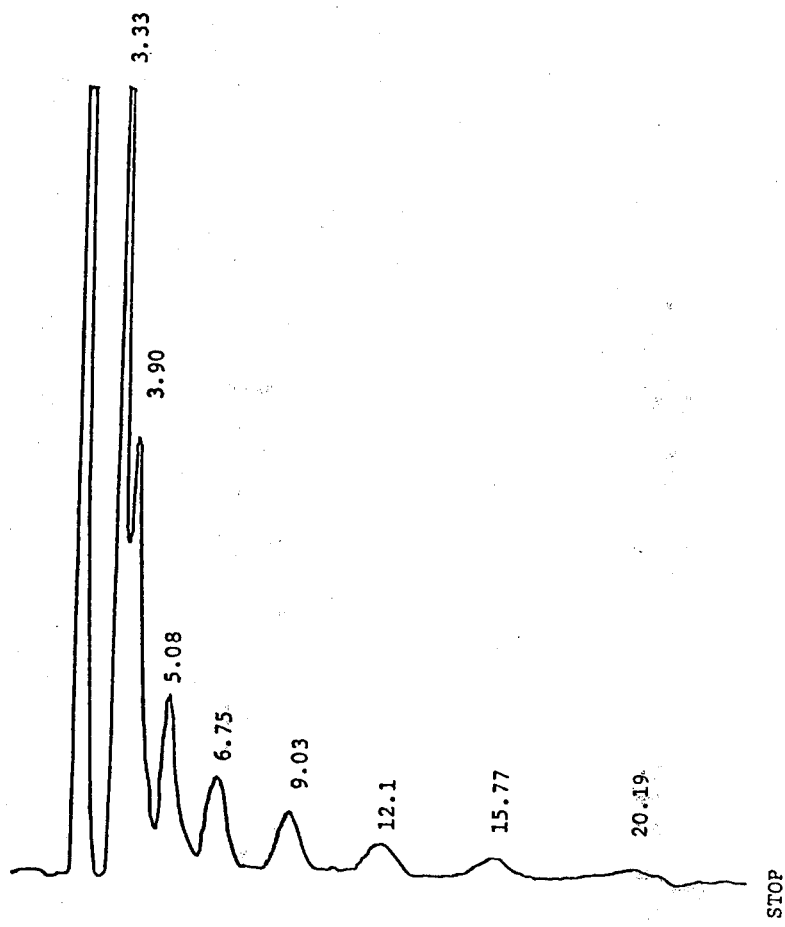
Figure 3:
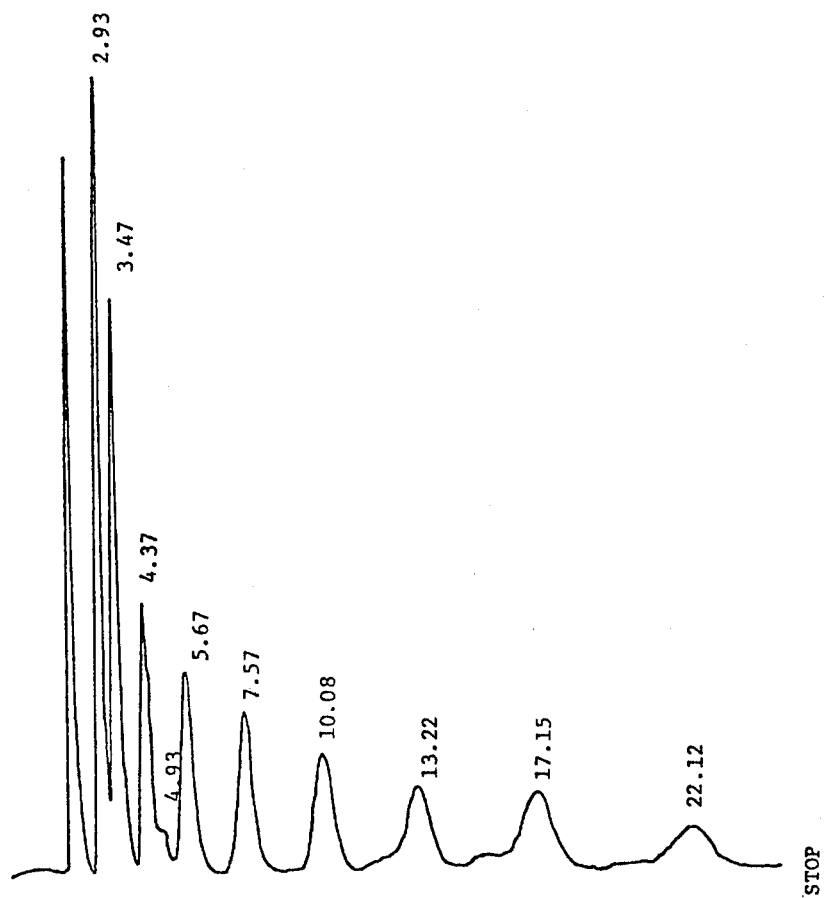
Figure 4:
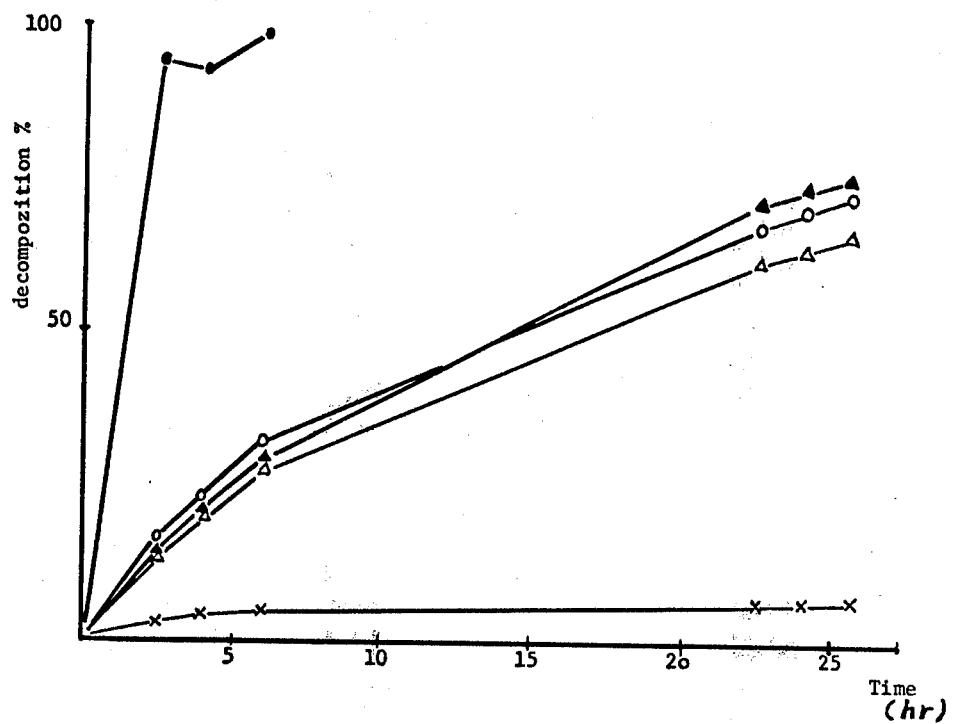
FIG. 4 shows decomposition ratios (%) of respective compounds obtained when N-methyloligoglycosyl-moranolines are reacted with α-1,4-glucanhydrolase, in which ●, —X—, —▲—, —Δ—, and ⦁ represent results of maltose, 4-(α-D-glucosyl)-N-methylmoranoline, 4-(α-D-maltosyl)-N-methylmoranoline, 4-(α-D-maltotriosyl)-N-methylmoranoline and 4-(α-D-maltotetraosyl)-N-methylmoranoline, respectively.
Figure 5:
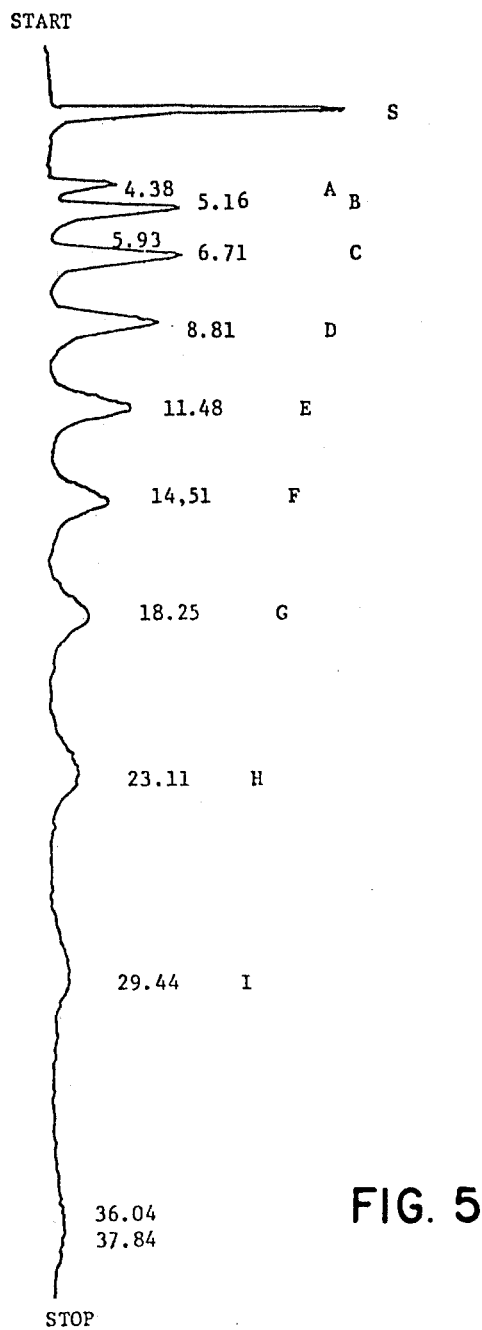
FIGS. 5 and 6 show the results of the high speed liquid chromatography (Model ALC/GPC-244 supplied by Waters Co.) before and after reaction with α-1,4-glucanglucohydrolase in Example 6 where the μ-Bondapack NH$_2$ column was used, acetonitrile/water (70/30) fed at a flow rate of 1.5 ml/min was used for the development and a chromatopac (Model C-R1A supplied by Shimadzu Seisakusho K.K.) was used for the analysis.
Figure 6:
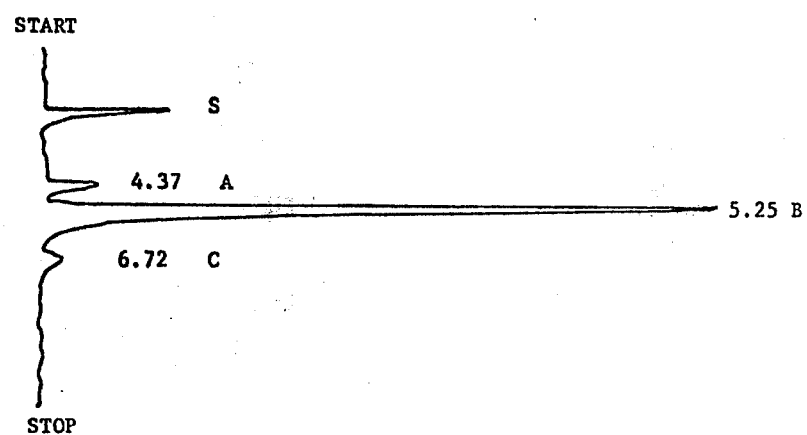

We claim:

1. A moranoline derivative of the formula:

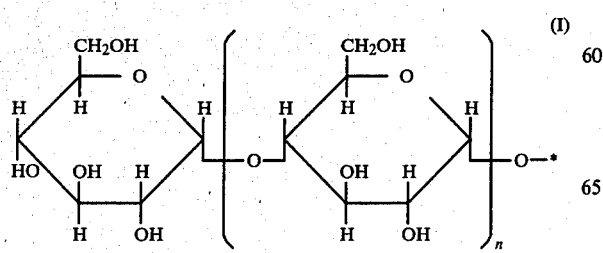

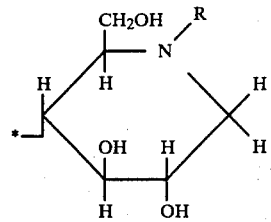

wherein n is an integer of from 0 to 7, and R is H or lower alkyl.

2. A process for the preparation of a moranoline derivative of the formula (I):

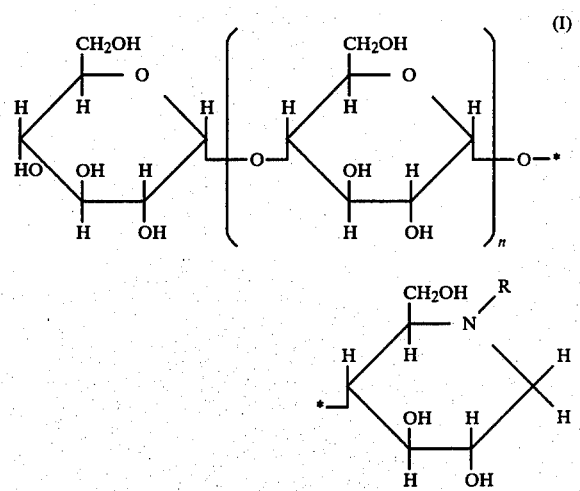

wherein R is H or lower alkyl, and n is an integer of from 1 to 7, which comprises reacting an aqueous solution containing a moranoline of the formula (II):

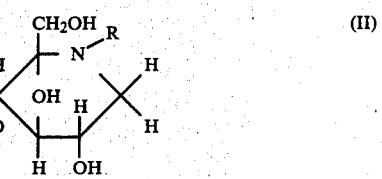

wherein R is as defined above and cyclodextrin or soluble starch with cyclodextrin glycosyltransferase to obtain a mixture containing a moranoline derivative of the formula (I) and isolating the mixture into respective components.

3. A process for the preparation of a glucosylmoranoline derivative of the formula

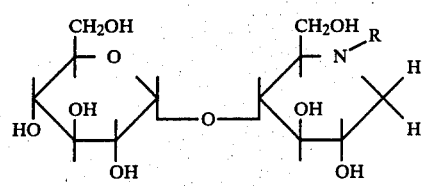

wherein R is hydrogen or lower alkyl, which comprises reacting a solution of a mixture containing a compound of the formula (I):

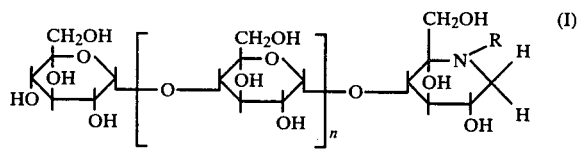

wherein R is as defined above and n is an integer of from 0 to 20, and a compound of the formula (IV):

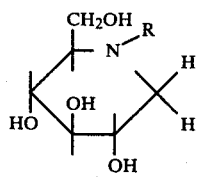

wherein R is as defined above, with the proviso that the case where a compound of the formula (I) in which n is zero is used alone as the compound of the formula (I) is excluded with α-1,4-glucan-glucohydrolase directly or after addition of a cation exchange resin.

4. A moranoline according to claim 1 wherein R is H.

5. A moranoline according to claim 1 wherein R is lower alkyl.

6. A moranoline according to claim 1 wherein n is zero.

7. A process according to claim 2 wherein the reaction temperature is about 40° C. and the pH is from 5.0 to 8.5 for a reaction time of 1 to 3 days.

8. A moranoline according to claim 1 wherein R is methyl.

9. A process according to claim 2 wherein R is methyl.

10. A process according to claim 3 wherein R is methyl.

11. A process according to claim 3 wherein a cation exchange resin is added, said cation exchange resin being a strongly acidic cation exchange resin.

* * * * *